(12) United States Patent
Seyama et al.

(10) Patent No.: US 12,089,824 B2
(45) Date of Patent: Sep. 17, 2024

(54) WEARABLE SENSING DEVICE

(71) Applicant: Nippon Telegraph and Telephone Corporation, Tokyo (JP)

(72) Inventors: Michiko Seyama, Tokyo (JP); Yujiro Tanaka, Tokyo (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 995 days.

(21) Appl. No.: 16/968,648

(22) PCT Filed: Feb. 20, 2019

(86) PCT No.: PCT/JP2019/006284
§ 371 (c)(1),
(2) Date: Aug. 10, 2020

(87) PCT Pub. No.: WO2019/176483
PCT Pub. Date: Sep. 19, 2019

(65) Prior Publication Data
US 2020/0405272 A1    Dec. 31, 2020

(30) Foreign Application Priority Data
Mar. 12, 2018 (JP) .................................. 2018-043806

(51) Int. Cl.
*A61B 10/00* (2006.01)
*G01N 33/487* (2006.01)
(52) U.S. Cl.
CPC ... *A61B 10/0064* (2013.01); *G01N 33/48707* (2013.01); *A61B 2217/005* (2013.01);
(Continued)

(58) Field of Classification Search
CPC . A61B 5/00; A61B 10/0064; A61B 2217/005; A61B 2560/0412;
(Continued)

(56) References Cited

U.S. PATENT DOCUMENTS

2018/0020966 A1* 1/2018 Begtrup .................... A61B 5/01
600/301
2018/0064377 A1* 3/2018 Rogers ................... B01L 3/5027
(Continued)

FOREIGN PATENT DOCUMENTS

JP          2017023408 A    *  2/2017
JP          2017198577 A    * 11/2017

OTHER PUBLICATIONS

Translation of JP 2017198577 A to Hano (Year: 2017).*
(Continued)

*Primary Examiner* — May A Abouelela
*Assistant Examiner* — Anna Roberts
(74) *Attorney, Agent, or Firm* — Slater Matsil, LLP

(57) ABSTRACT

A suction channel is made of a flexible resin, and is formed in a base. The suction channel suctions sweat that has come into contact with the detection electrode. The suction channel makes use of surface tension from micro channels to suction liquid into an interior from a suction port. A sodium ion detection electrode, a potassium ion detection electrode, and a reference electrode, which are detection electrodes for detecting ions contained in the sweat, are formed on an inner wall of a channel of the suction channel.

16 Claims, 1 Drawing Sheet

(52) U.S. Cl.
CPC .......... *A61B 2560/0412* (2013.01); *A61B 2560/0431* (2013.01)

(58) Field of Classification Search
CPC .... A61B 2560/0431; G01N 1/10; G01N 1/12; G01N 27/26; G01N 27/28; G01N 27/416; G01N 33/48707; G01N 33/50; G01N 33/84; G01N 37/00
USPC ................................................ 600/346, 573
See application file for complete search history.

(56) References Cited

U.S. PATENT DOCUMENTS

| | | | |
|---|---|---|---|
| 2019/0008448 A1* | 1/2019 | Begtrup | G01N 33/48792 |
| 2020/0129112 A1* | 4/2020 | Model | G16H 20/00 |
| 2022/0072753 A1* | 3/2022 | McAlpine | B33Y 30/00 |

OTHER PUBLICATIONS

Yuto, Kato, et al., "Development of a Sweat Lactic Acid Sensor Using an Elastic Biofuel Cell," The 63 Spring Academic Lecture Series of the Japan Society of Applied Physics, 2 pages, Mar. 19, 2016.

Baker, L. B. et al., "Comparison of Regional Patch Collection vs. Whole Body Washdown for Measuring Sweat Sodium and Potassium Loss During Exercise," J Appl Physiol, Jun. 17, 2009, 887-895, vol. 107, American Physiological Society.

Gao, W. et al., Fully Integrated Wearable Sensor Arrays for Multiplexed in Situ Perspiration Analysis, NATURE, Jan. 28, 2016, pp. 509-526, vol. 529, Macmillian Publishers Limited.

* cited by examiner

WEARABLE SENSING DEVICE

CROSS-REFERENCE TO RELATED APPLICATIONS

This application is a national phase entry of PCT Application No. PCT/JP2019/006284, filed on Feb. 20, 2019, which claims priority to Japanese Application No. 2018-043806, filed on Mar. 12, 2018, which applications are hereby incorporated herein by reference.

TECHNICAL FIELD

The present invention relates to a wearable sensing device that detects ions contained in sweat.

BACKGROUND

Dehydration is a symptom that often appears in hyperthermia disorders commonly referred to as heat stroke. The number of heat stroke cases increases in a hot summer period, and in Japan, heat stroke occurs commonly "at home", followed by "while at work" and "while exercising". By gender and age, the incidence of elderly people "at home" is high, and it occurs "while exercising" in both men and women in the young generation and "while at work" in adult men who apparently tend to work in a high-temperature environment. Severe heat stroke can lead to death, and even in winter when the temperature drops, people can be dehydrated and may be taken to hospital by ambulance. Occurrence of these dehydration symptoms can be suppressed if the condition of a person can be grasped and the surrounding environment, food and drink, and the like are properly adjusted.

The reason why the incidence rate of the elderly indoors is high could be that they are in a state of being insensitive to and unable to notice by themselves changes in their body as they age. This is a problem also common to those who have impaired thermoregulatory function due to injuries of the cervical spine or the like. In addition, infants, who cannot easily express their intention relative to their own change, may have progressed dehydration without being noticed by an attendant even if there was any. For workers who are performing work, it is desirable to implement measures such as securing drinking water and cooling in an efficient manner and at a necessary timing so as not to hinder the progress of their work. Therefore, if there is a sensor device that can readily measure dehydration, the occurrence of dehydration can be prevented, making it possible to respond before a critical situation is caused.

As a common method for readily measuring whether a person is dehydrated or not, there is a technique for measuring an amount of sweat that evaporates from or flows out of the skin. This technique determines a color that appears when sweat is absorbed in order to determine an amount of water in sweat by allowing sweat to be absorbed in a filter paper or the like with the filter paper or the like used containing dye that develops color in the presence of water. In this method, though an amount of perspiration can be grasped and intake of drinking water can be prompted according to it, it is considered difficult to identify when dehydration is actually about to occur, that is, a phenomenon in which it is difficult to perspire.

In dehydration, the index as important as the amount of sweat is the concentrations of sodium ions and potassium ions. Potassium is present as ions in human intracellular fluid, and sodium is present as ions in human extracellular fluid. In accordance with the osmotic pressure generated by the difference between the concentrations of these ions, water in the intracellular fluid travels to the extracellular fluid so that a human blood volume is generally maintained at approximately 1/13 of the body weight. When dehydration begins to occur and 10% of the blood volume is lost, the condition is considered mild dehydration, and the condition with a 30% loss thereof is said to represent dehydration potentially involving risk.

When a large amount of sweat is released in a high-temperature environment, it is difficult for a fluid to flow from the intracellular fluid to the extracellular fluid, which results in a condition of increased sodium concentration while the potassium concentration does not change. When this happens, there is no osmotic pressure difference because the salt concentration in the extracellular fluid increases, and as a result, the extracellular fluid volume does not increase, nor does the blood volume. Although the blood serves like a radiator by circulating to lower the body temperature, the effect of lowering the body temperature cannot also be obtained because the blood volume does not rise.

As a countermeasure against heat stroke as described above, there is a report with regards to ion concentration in sweat using a wearable device equipped with an ion sensor (Non-Patent Literature 2).

Note that the concentration of ions in sweat varies among different individuals, and particularly, that of sodium ions greatly differs depending on the condition of dehydration as well as the state until dehydration occurs as described above. For example, Non-Patent Literature 2 discloses that the ion concentrations in human sweat collected under a high-temperature environment from five subjects are 29-37, 56-101, 55-107, 75-117, 67-127 (mEq/L) for Na ions, and 2.8-3.7, 3.1-4.6, 3.6-5.1, 4.7-5.9, 4.4-5.3 mEq/L for K ions.

A large number of potassium ions are present in the intracellular fluid, and though the concentration of potassium ions does fluctuate in plasma, the concentration fluctuation thereof is much smaller than that of sodium ions. Here, Eq (milliequivalent) is a unit representing an electrolytic mass, and is represented by the amount of substance (mol)×the valence of ion. Na and K are both monovalent ions, and the above unit is equivalent to the mol.

CITATION LIST

Non-Patent Literature

Non-patent literature 1: W. Gao et al., "Fully integrated wearable sensor arrays for multiplexed in situ perspiration analysis", NATURE, vol. 529, pp. 509-514, 2016.
Non-patent literature 2: L. B. Baker, et al., "Comparison of regional patch collection vs. whole body washdown for measuring sweat sodium and potassium loss during exercise", J. Appl. Physiol., vol. 107, pp. 887-895, 2009.

SUMMARY

Technical Problem

Meanwhile, the concentration of ions contained in sweat depends on the concentration of ions in the blood of an individual. Therefore, even in the physiologically normal range, the concentration is expected to vary among individuals at the level of several tens of mM. From these facts, in determining dehydration as described above, it is important to measure the concentration of ions contained in sweat at the time of perspiration with accuracy. By contrast, in the technique using the above-described conventional wearable device, sweat from perspiration accumulates at a position of an ion sensor over time. For this reason, in the technique described above, what is detected is the concentration of ions of the accumulated sweat, which is different from the concentration of ions contained in sweat produced at the time of detection.

As described above, though it is conceivable that the condition of a human body such as heat stroke can be grasped by measuring the concentration of ions contained in sweat, there is a problem in the conventional art that the concentration of ions contained in sweat at the time when sweat is produced cannot be measured with accuracy.

Embodiments of the present invention have been made to solve the above problem, and it is an object thereof to enable higher-accuracy measurement of the concentration of ions contained in sweat at the time when sweat is produced.

Means for Solving the Problem

A wearable sensing device according to embodiments of the present invention includes a sheet-like base made of a flexible resin, a suction channel made of a flexible resin and formed in the base for suctioning sweat from a suction port formed in the base, a detection electrode configured to contact the sweat suctioned from the suction port for detecting ions contained in the sweat, a measurement chip for performing measurement of a concentration of the ions by electrochemical measurement making use of the detection electrode, and a battery serving as a power supply for the measurement chip.

which is disposed in the suction channel at a predetermined distance from the suction port of the suction channel and develops color by contact with water, is provided, and the base and the suction channel are made of a transparent resin.

In the wearable sensing device, the suction channel is formed integrally with the base.

In the wearable sensing device, the detection electrode includes a sodium ion detection electrode for detecting sodium ions, and a potassium ion detection electrode for detecting potassium ions.

In the wearable sensing device, the measurement chip is equipped with a communication function for transmitting a measurement result.

In the wearable sensing device, the measurement chip and the battery are formed on the base.

Effects of Embodiments of the Invention

As described above, according to embodiments of the present invention, since the suction channel is provided, an excellent effect is obtained that the concentration of ions contained in sweat at the time when sweat is produced can be measured with higher accuracy.

DETAILED DESCRIPTION OF ILLUSTRATIVE EMBODIMENTS

Figure 1A:
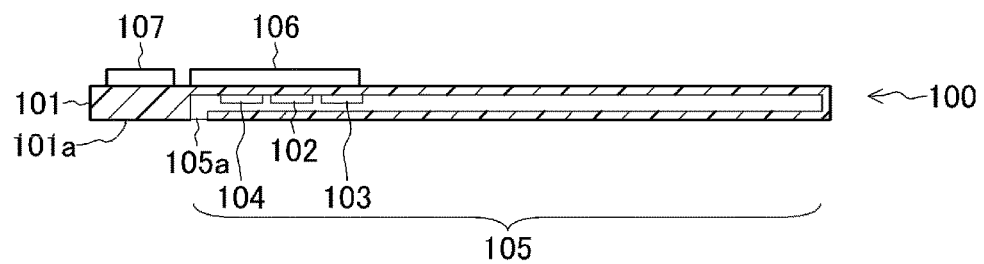
FIG. 1A is a cross-sectional view showing a structure of a wearable sensing device 100 in an embodiment of the present invention.
Figure 1B:
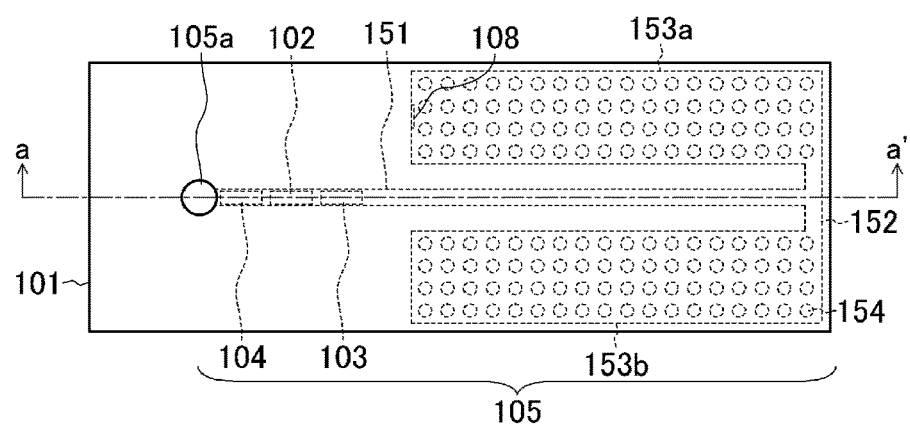
FIG. 1B is a cross-sectional view showing a partial structure of the wearable sensing device 100 in an embodiment of the present invention.

Hereinafter, a wearable sensing device 100 according to an embodiment of the present invention will be described with reference to FIGS. 1A and 1B. The wearable sensing device 100 includes a base 101, a sodium ion detection electrode 102, a potassium ion detection electrode 103, a reference electrode 104, a suction channel 105, a measurement chip 106, and a battery 107. Note that FIG. 1A shows a cross section taken along the line a-a' of FIG. 1B.

The base 101 is made of a flexible resin, and is formed in the shape of a sheet. The base 101 can be wrapped around, for example, a forearm, an upper arm, a wrist, or the like. A contact surface 101a of the base 101 is a surface that contacts a skin of a human body. The base 101 is attached to a human body by bringing the contact surface 101a into contact with a skin of a human body.

The sodium ion detection electrode 102, the potassium ion detection electrode 103, and the reference electrode 104 are configured to contact the sweat suctioned from a suction port 105a of the suction channel 105. They are detection electrodes for detecting ions contained in the sweat.

The suction channel 105 is made of a flexible resin and is formed in the base 101. The suction channel 105 suctions sweat secreted from sweat glands in the skin of a human body to which it is attached. The suction channel 105 is formed integrally with the base 101. The suction channel 105 makes use of surface tension of micro channels, which is well known, to suction liquid into an interior from the suction port 105a which is formed on the contact surface 101a of the base 101. The speed at which sweat is suctioned can be adjusted by designing of a width, height, and the like of the channel.

Figure 2:
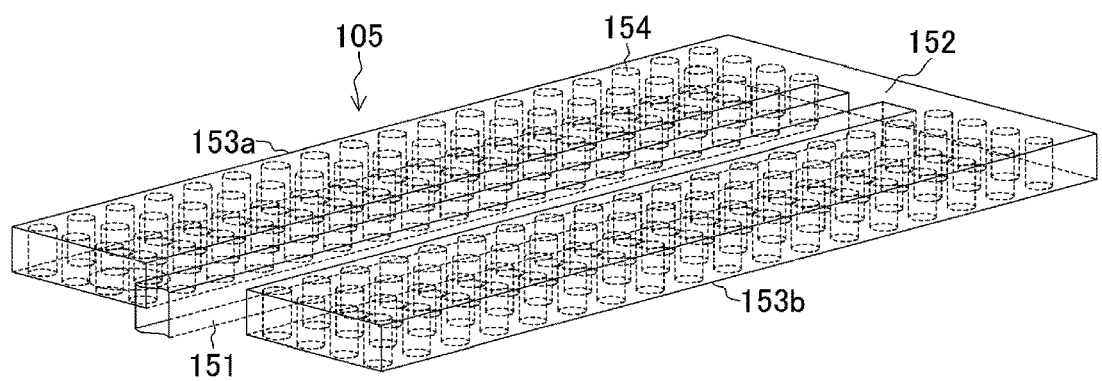
FIG. 2 is a perspective view showing a partial structure of the wearable sensing device 100 in an embodiment of the present invention.

As shown in FIG. 2, the suction channel 105 includes the suction port 105a, a channel 151, a branch channel 152, and suction units 153a and 153b. The suction port 105a is open to the contact surface 101a. The channel 151 communicates the suction port 105a with the branch channel 152. The branch channel 152 communicates the channel 151 with the suction units 153a and 153b. In the embodiment, the suction port 105a and the suction units 153a and 153b communicate each other through the channel 151 and the branch channel 152. In addition, a plurality of columnar units 154 connecting a floor surface and a ceiling surface thereof are formed in the suction units 153a and 153b.

Here, cross-sectional dimensions of the channel 151 and the branch channel 152 are in a range in which capillary action occurs with respect to liquid. Moreover, the distance between the floor surface and the ceiling surface of the suction units 153a and 153b is such that a liquid that has infiltrated the suction units 153a and 153b can contact both surfaces at the same time. In addition, the distance between the adjacent columnar units 154 of the suction units 153a and 153b is such that a liquid that has infiltrated the suction units 153a and 153b can contact both units at the same time.

According to the suction channel 105 described above, the sweat that has reached the suction port 105a is taken up into the suction units 153a and 153b through the channel 151 and the branch channel 152 by capillary action. Here, the sodium ion detection electrode 102, the potassium ion detection electrode 103, and the reference electrode 104 are formed on an inner wall of the channel 151. The sweat taken into the channel 151 by the suction port 105a passes through the sodium ion detection electrode 102, the potassium ion detection electrode 103, and the reference electrode 104 in contact therewith.

The number of the suction units 153a and 153b is not limited to two, and by increasing the capacity with a structure in which more suction units are connected, sweat can be suctioned in a continuous manner for a longer time. Furthermore, in the embodiment, the suction speed can be changed by the height of the columnar unit 154 (the distance between the floor surface and the ceiling surface). Additionally, a groove that does not communicate with the suction units 153a and 153b from the suction port 105a may be formed. With this groove, when a large amount of sweat is produced, sweat too much for measurement may be quickly discharged to the outside.

The measurement chip 106 performs measurement of the concentration of ions by electrochemical measurement making use of the detection electrode. Further, in the embodiment, the measurement chip 106 is equipped with a communication function for transmitting a measurement result. In the embodiment, the measurement chip 106 is formed (mounted) in contact with the base 101.

The battery 107 serves as a power supply for the measurement chip 106. The battery 107 includes, for example, an air battery. In the embodiment, the battery 107 is formed in contact with the base 101. For example, when a coating layer for protecting the wearable sensing device 100 before it is used is removed for use, the battery 107 sealed with the coating layer is brought into contact with the air, starting power generation and then power supply to the measurement chip 106.

The measurement chip 106, which has been in an operating state with the start of power supply from the battery 107, for example, transmits a connection request signal for wireless communication. The connection request signal is received, for example, by a portable terminal device not shown, resulting in a wireless connection established between the measurement chip 106 and the portable terminal device.

Furthermore, the measurement chip 106 in an operating state obtains the concentrations of sodium ions and potassium ions. The sodium ions and the potassium ions are detected when the sweat taken into the channel 151 by the suction port 105a has reached the sodium ion detection electrode 102, the potassium ion detection electrode 103, and the reference electrode 104. Further, the measurement chip 106 transmits an obtained value of each ion concentration to the portable terminal device. The portable terminal device, which has received the measured value of each ion concentration, issues an alert concerning dehydration by sound, display, or the like. The portable terminal device issues the alert by comparing the value of each ion concentration with the reference concentration value or the like through operation of an installed application software.

According to the embodiment described above, the sweat that is secreted from sweat glands by perspiration and reaches the suction port 105a is taken up into the suction units 153a and 153b via the channel 151 of the suction channel 105. Therefore, even when a large amount of sweat is generated, it does not stay at a position of the detection electrode nor accumulate. For this reason, according to the embodiment, sweat coming into contact with the detection electrode can be limited to the sweat immediately after perspiration (secretion). As a result, according to the embodiment, the concentration of ions contained in sweat at the time when (immediately after) sweat is produced can be measured with higher accuracy. Furthermore, according to the embodiment, a time-series change in a component of sweat from perspiration can be observed.

In addition, an indicator layer 108 carrying an indicator that develops color by contact with water may be disposed in the suction channel at a predetermined distance from the suction port 105a of the suction channel 105. The indicator layer 108 can be disposed at a point where liquid (sweat) suctioned by the suction channel 105 reaches at the end. The indicator is, for example, cobalt chloride. In this case, the base 101 and the suction channel 105 are made of a transparent resin. When the sweat suctioned by the suction channel 105 reaches the indicator layer 108, the indicator layer 108 develops color (changes color). By confirming the color development of the indicator layer 108, occurrence of a predetermined amount of perspiration can be grasped.

Embodiment

Hereinafter, a more detailed description will be given by use of the embodiment. First, a fabrication of the wearable sensing device 100 will be briefly described. First, a support sheet made of polydimethylsiloxane (PDMS) is prepared. The support sheet is made of, for example, hydrophilic PDMS. Next, electrode patterns made of Au are formed on an electrode forming surface of the support sheet at positions where the sodium ion detection electrode 102, the potassium ion detection electrode 103, and the reference electrode 104 are to be formed. The electrode pattern is formed by depositing Au, for example, by a sputtering method using a stencil mask or the like. The electrode pattern is formed at a position where the channel 151 of the suction channel 105 is disposed.

Next, a silver-silver chloride layer is formed on the formed electrode pattern. Then, the sodium ion detection electrode 102 is obtained by dropping and drying a vinyl chloride-based cocktail containing an ionophore of sodium ions onto one of the three electrode patterns. Further, the potassium ion detection electrode 103 is obtained by dropping and drying a vinyl chloride-based cocktail containing an ionophore of potassium ions onto one of the remaining two electrode patterns. The remaining one electrode pattern is the reference electrode 104. At the time when respective electrodes are thus formed, a pseudo sweat component may be brought into contact with the sodium ion detection electrode 102 and the potassium ion detection electrode 103 to condition surfaces of these detection electrodes.

Next, a channel sheet made of PDMS is formed. The channel sheet is obtained, for example, by forming a mold having a channel structure of the part to be the suction channel 105, on which a hydrophilic PDMS film is formed (applied), which is heated under predetermined heating conditions to be hardened (solidified) and released from the mold. On the channel sheet, a groove structure to serve as respective channels and the suction units 153a and 153b, as well as the columnar units 154 are formed. By laminating the channel sheet thus formed and the support sheet, the base 101 in which the suction channel 105 is integrally formed is obtained. A bonding surface on the electrode forming surface of the support sheet is laminated to a bonding surface on a groove forming side of the channel sheet.

The support sheet is laminated to the channel sheet at a side where the groove structure is formed. In this lamination, a layer made of hydrophobic PDMS is preferably formed on each lamination surface. This lamination allows the respective bonding surfaces to be mutually bonded by a selfadhesive force of PDMS. Note that the suction port 105a is formed in advance in the support sheet.

According to the base 101 described above, since a surface in contact with a skin and an interior of each channel of the suction channel 105 are hydrophilic, sweat is not repelled, which allows the suction channel 105 to efficiently carry out suction of sweat utilizing a capillary force. Furthermore, since the lamination surface is hydrophobic, sweat suctioned into each suction channel can be prevented from leaking out from a lamination interface.

Next, after the base 101 having respective detection electrodes and the suction channel 105 has been formed as described above, a predetermined wiring pattern is also formed by the sputtering method or the like as mentioned above. By using a metal colloid solution, for example, to form a wiring pattern, wiring with the measurement chip 106 and the battery 107 is executed.

The base 101 is attached to a human body by bringing the contact surface 101a of the base 101 described above into contact with a skin. When sweat generated by perspiration reaches the suction port 105a, it is taken into the channel 151. Then, the sweat reaches the sodium ion detection electrode 102, the potassium ion detection electrode 103, and the reference electrode 104. Next, the sweat proceeds inside the channel 151 and the branch channel 152 by a capillary force, and reaches the suction units 153a and 153b. The sweat that has reached the suction units 153a and 153b is suctioned between a plurality of columnar units 154 having a diameter of 100 μm and a height of approximately 100 μm (for example, 300 μm), for example.

Figure 3:
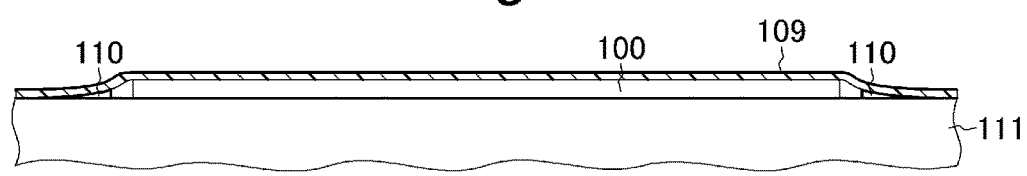
FIG. 3 is a cross-sectional view showing a structure of the wearable sensing device 100 in an embodiment of the present invention.

Note that the wearable sensing device 100 may be attached to a surface of a skin 111 while being covered by a cover 109, as shown in FIG. 3. The cover 109 is patched to the surface of the skin 111 with an adhesive layer no provided on a periphery. Before being used, the wearable sensing device 100 is attached to a release paper not shown, and the wearable sensing device 100 is wrapped with the release paper and the cover 109.

When in use, the wearable sensing device 100 is peeled off from the release paper, and the contact surface 101a is attached to a part of the skin 111 where sweat is released. If the battery 107 is an air battery, a cover sealing an air electrode of the air battery may be peeled off at the same time of releasing from the release paper. By doing so, when the wearable sensing device 100 is peeled off from the release paper, as described above, power supply from the battery 107 is started, which makes the measurement chip 106 start operation, bringing it into a measurement state.

The produced sweat reaches and is suctioned into the suction port 105a, and reaches the sodium ion detection electrode 102, the potassium ion detection electrode 103, and the reference electrode 104 provided in the channel 151. When the amount thereof becomes sufficient (approximately 0.7 μL), the concentration of ions contained in the sweat is measurable. In this measurement, the measured ion concentration is displayed on the portable terminal device.

For example, approximately 20 minutes from the start of measurement is an adjustment time, and after the adjustment time, for example, dehydration can be determined using a measurement result. If a measured concentration of each ion deviates from a set normal state, for example, the condition is determined as dehydration. Furthermore, if a measured sodium ion concentration is equivalent to or less than 10 mEq/L, a low sodium symptom or the like is suspected and an alert thereof may be issued.

When the alert is issued, there is a risk of an abnormal state such as dehydration. Therefore, it is desired to immediately move to a cool dark place, suspend activity, consume drinking water, or the like. Furthermore, when a low sodium symptom is suspected, it is desirable to consume a beverage containing salt.

As described above, according to embodiments of the present invention, since the suction channel is provided, a concentration of ions contained in sweat at the time when sweat is produced can be measured with higher accuracy. According to the wearable sensing device of embodiments of the present invention, a risk of dehydration can be notified, for example, based on the ion concentrations of components of sweat when a person is perspiring in an active state. By doing so, not only a person to whom the wearable sensing device is attached can recognize dehydration that is being caused without being noticed by the person himself/herself, but another person who is attending or who is at a distance can also be notified of the risk of dehydration. Furthermore, by realizing quickly a risk of dehydration, preventive measures can be taken before a severe symptom develops.

Note that the present invention is not limited to the embodiment described above, and it is apparent that many modifications and combinations can be made by those skilled in the art without departing from the technical concepts of the present invention.

REFERENCE SIGNS LIST

100 Wearable sensing device
101 Base
101a Contact surface
102 Sodium ion detection electrode
03 Potassium ion detection electrode
104 Reference electrode
105 Suction channel
105a Suction port
106 Measurement chip
107 Battery
108 Indicator layer
151 Channel
152 Branch channel
153a, 153b Suction units
154 Columnar unit

The invention claimed is:

1. A wearable sensing device comprising:
   a base made of a first flexible resin;
   a suction channel in the base, the suction channel being made of a second flexible resin, and the suction channel being configured to suction sweat from a suction port in the base using a branch channel connecting the suction channel to suction regions disposed in the base at opposite sides of the suction channel;
   a plurality of detection electrodes configured to contact the sweat suctioned from the suction port and detect ions contained in the sweat;
   a measurement chip configured to measure, by electrochemical measurement, a concentration of the ions detected by each of the detection electrodes, wherein an entirety of the measurement chip overlaps the suction port and the plurality of detection electrodes without overlapping the branch channel or the suction regions; and
   a battery serving as a power supply for the measurement chip.

2. The wearable sensing device according to claim 1, further comprising:

an indicator in the suction channel at a predetermined distance from the suction port, wherein the indicator is configured to develop a color by contact with water, and wherein the base and the suction channel are each made of a transparent resin.

3. The wearable sensing device according to claim 1, wherein the suction channel is integral with the base.

4. The wearable sensing device according to claim 1, wherein the detection electrodes comprise:
 a sodium ion detection electrode for detecting sodium ions; and
 a potassium ion detection electrode for detecting potassium ions.

5. The wearable sensing device according to claim 1, wherein the measurement chip is equipped with a communication function for transmitting a measurement result of the measurement chip.

6. The wearable sensing device according to claim 1, wherein the measurement chip and the battery are disposed on the base.

7. The wearable sensing device according to claim 1, wherein the base has a sheet-like shape.

8. The wearable sensing device according to claim 1, wherein the battery is disposed at a first end of the base in a position not overlapping the suction channel or any of the detection electrodes.

9. The wearable sensing device according to claim 1, further comprising a plurality of columnar structures in the suction regions, each of the columnar structures connecting a floor surface and a ceiling surface of the suction regions.

10. A method comprising:
 suctioning, by a suction channel, sweat from a suction port in a base using a branch channel connecting the suction channel to suction regions disposed in the base at opposite sides of the suction channel, wherein the base is made of a first flexible resin, and wherein the suction channel is made of a second flexible resin;
 contacting, by a plurality of detection electrodes, the sweat suctioned from the suction port;
 detecting, by each of the detection electrodes, ions contained in the sweat; and
 measuring, by a measurement chip connected to each of the detection electrodes and by electrochemical measurement, a concentration of the ions detected by each of the detection electrodes, wherein an entirety of the measurement chip overlaps the suction port and the plurality of detection electrodes without overlapping the branch channel or the suction regions.

11. The method of claim 10, wherein the base, the suction channel, each of the detection electrodes, and the measurement chip are comprised in a wearable sensing device, and wherein the wearable sensing device further comprises a battery serving as a power supply for the measurement chip, the battery being disposed at a first end of the base in a position not overlapping the suction channel or any of the detection electrodes.

12. The method of claim 11, wherein the wearable sensing device further comprises an indicator in the suction channel, wherein the indicator develops a color by contact with water, and wherein the base and the suction channel are each made of a transparent resin.

13. The method of claim 10, wherein the suction channel is formed integrally with the base.

14. The method of claim 10, wherein the detection electrodes comprise:
 a sodium ion detection electrode for detecting sodium ions; and
 a potassium ion detection electrode for detecting potassium ions.

15. The method of claim 10, further comprising:
 transmitting, by the measurement chip, a measurement result of the measurement chip.

16. The method of claim 10, wherein suctioning the sweat further comprises generating a capillary action using a plurality of columnar structures disposed in the suction regions, each of the columnar structures connecting a floor surface and a ceiling surface of the suction regions.

* * * * *